US00PP32966P3

(12) United States Plant Patent
Knapp et al.

(10) Patent No.: US PP32,966 P3
(45) Date of Patent: Apr. 13, 2021

(54) STRAWBERRY PLANT NAMED 'UCD VICTOR'

(50) Latin Name: ***Fragaria* x *ananassa* Duchesne**
Varietal Denomination: UCD Victor

(71) Applicant: The Regents of the University of California, Oakland, CA (US)

(72) Inventors: Steven J. Knapp, Davis, CA (US); Glenn S. Cole, Davis, CA (US); Douglas V. Shaw, Davis, CA (US); Kirk D. Larson, Santa Ana, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/501,372

(22) Filed: Apr. 1, 2019

(65) Prior Publication Data

US 2019/0380243 P1 Dec. 12, 2019
US 2020/0178444 P9 Jun. 4, 2020

Related U.S. Application Data

(60) Division of application No. 15/932,994, filed on Jun. 7, 2018, which is a continuation of application No. 15/530,135, filed on Dec. 6, 2016, now abandoned, which is a continuation of application No. 14/545,653, filed on Jun. 3, 2015, now abandoned.

(60) Provisional application No. 61/999,632, filed on Jul. 30, 2014, provisional application No. 61/997,548, filed on Jun. 4, 2014.

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208
CPC ..... A01H 6/7409
See application file for complete search history.

(56) References Cited

PUBLICATIONS

Trademark notice of 'Victor', downloaded on Mar. 15, 2020.*

* cited by examiner

*Primary Examiner* — Anne Marie Grunberg
(74) *Attorney, Agent, or Firm* — Kilpatrick Townsend & Stockton LLP

(57) ABSTRACT

'UCD Victor' is a short-day cultivar of a strawberry plant that is highly resistant to *Fusarium* wilt, and produces firm fruit and high yields of high quality, long shelf-life fruit.

6 Drawing Sheets

Genus and species: The strawberry cultivar of this invention is botanically identified as *Fragaria* x *ananassa* Duchesne.

Variety denomination: The variety denomination is 'UCD Victor'.

BACKGROUND OF THE INVENTION

This invention relates to a new and distinct short-day strawberry cultivar designated as 'UCD Victor', which originated from a cross performed in the winter of 2011 between proprietary germplasm parents 08C182P002 (unpatented) and 08C138P002 (unpatented). Seeds of the cross were harvested from greenhouse-grown plants in the spring of 2011 and germinated in June 2011. Seedlings were transplanted to a greenhouse in July 2011 and transplanted to the field in October 2011. 'UCD Victor' was selected and clones were first harvested in 2012. 'UCD Victor' has been asexually propagated since 2012.

The plant of this selection was originally designated '11C057P001' (also represented as '11.57-1') and later called '16SD045' or 'UC45' for evaluation in field trials. The variety was also called 'UC-26' in certain testing trials.

BRIEF SUMMARY OF THE INVENTION

'UCD Victor' is a short-day strawberry cultivar selected for increased marketable fruit yield, fruit firmness, extended shelf-life, and its resistance to Fusarium wilt. 'UCD Victor' is highly resistant to *Fusarium* wilt. The yields of the variety are significantly greater than 'San Andreas' (U.S. Plant Pat. No. 19,975) and 'Petaluma' (U.S. Plant Pat. No. 26,683); and comparable to 'Fronteras' (U.S. Plant Pat. No. 26,709). The fruits of 'UCD Victor' are firmer than the fruits of 'Fronteras' and 'UCD Warrior' (U.S. Plant patent application Ser. No. 16/501,373). 'UCD Victor' also has a more compact plant architecture compared to 'Fronteras'. 'UCD Victor' has enhanced *Fusarium* resistance compared to parent 008C182P002, and is more compact and has firmer fruit compared to parent 08C138P002.

'UCD Victor' was genotyped with a 35,000-SNP array (Hardigan et. al., *Plant Genome* 11:180049, 2018). The variety has a unique DNA profile compared to 'UCD Warrior', 'Fronteras', 'Petaluma' and 'San Andreas'. The pairwise genetic distances between 'UCD Victor' and 'UCD Warrior', 'Fronteras', 'Petaluma' and 'San Andreas' are estimated to be 0.267, 0.266, 0.253, and 0.299, respectively based on the 35,000-SNP genotype analysis. 'UCD Victor' also has a unique DNA profile compared to each of its parents, proprietary germplasm varieties 08C182P002 and 08C138P002.

'UCD Victor' is maintained by annual asexual propagation by stolons in Winters, Calif.

BRIEF DESCRIPTION OF THE DRAWINGS

The colors in the photograph are depicted as nearly true as is reasonably possible to obtain in color reproductions of this type.

DETAILED DESCRIPTION OF THE INVENTION

Fruit Production

Figure 1:
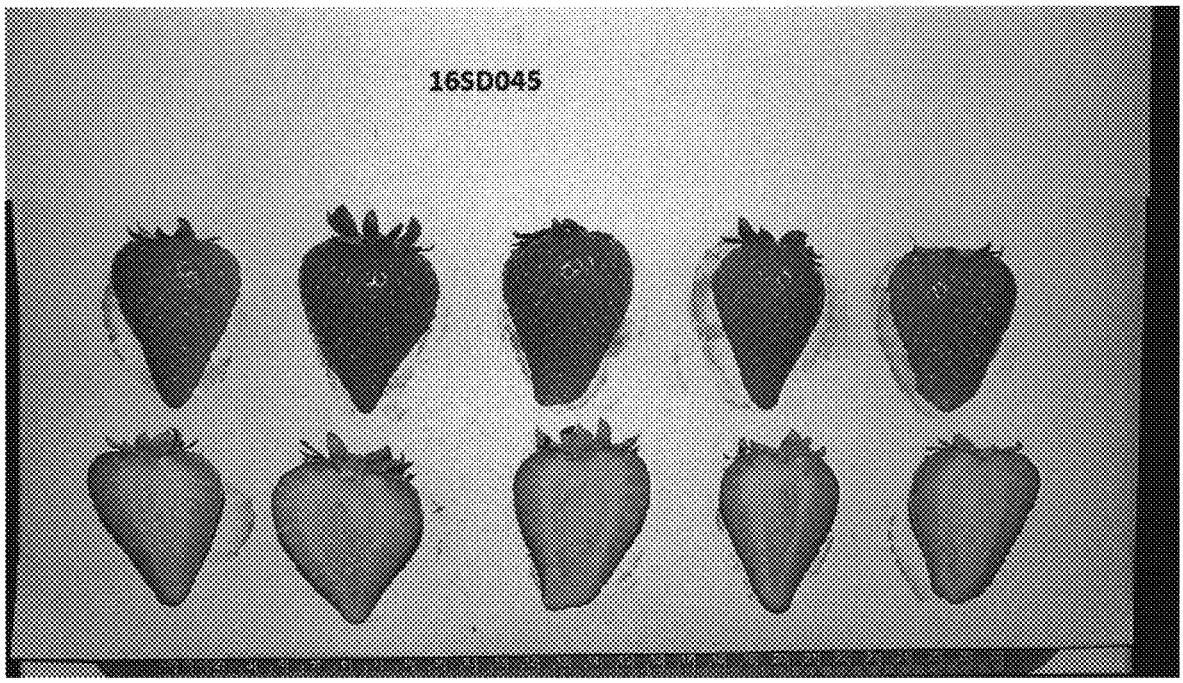
FIG. 1 shows fruit of 'UCD Victor' in cross-section.
Figure 2:
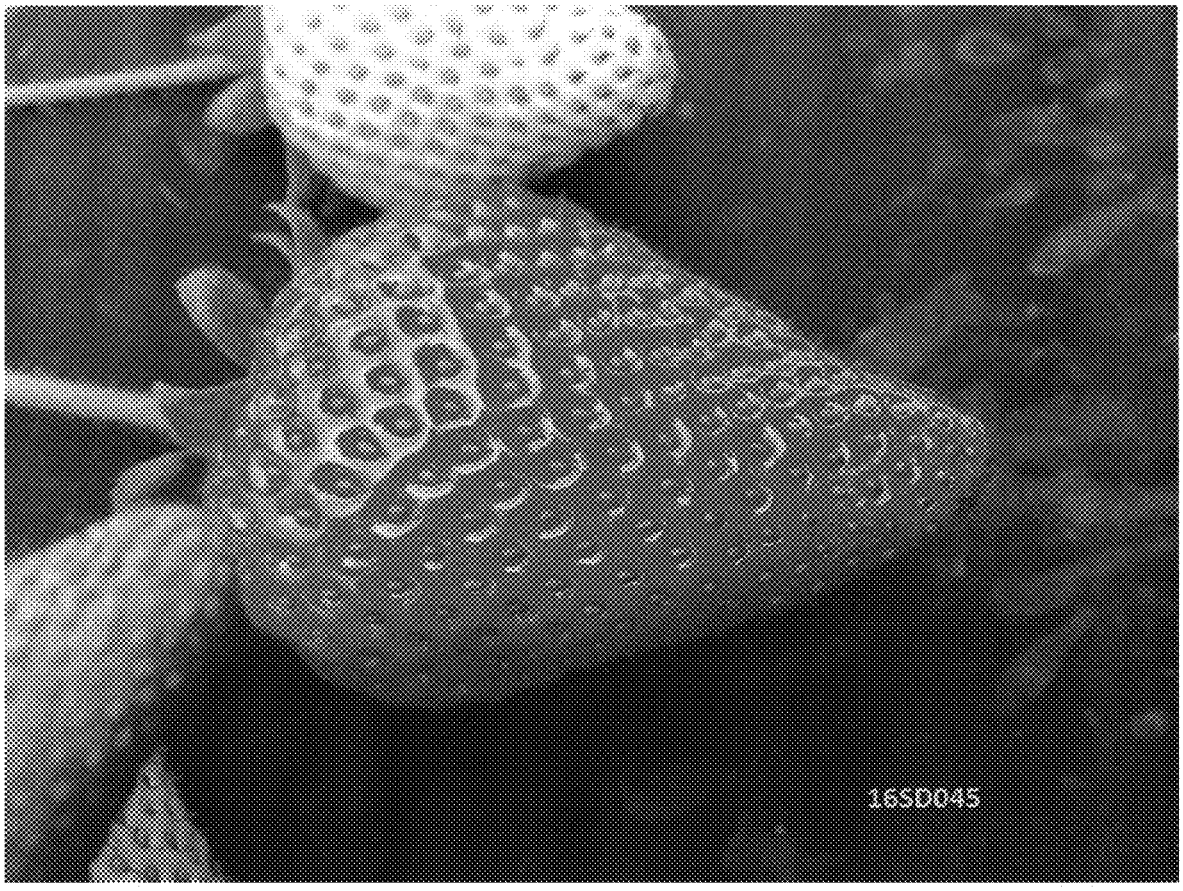
FIG. 2 illustrates color of the fruit.
Figure 3:
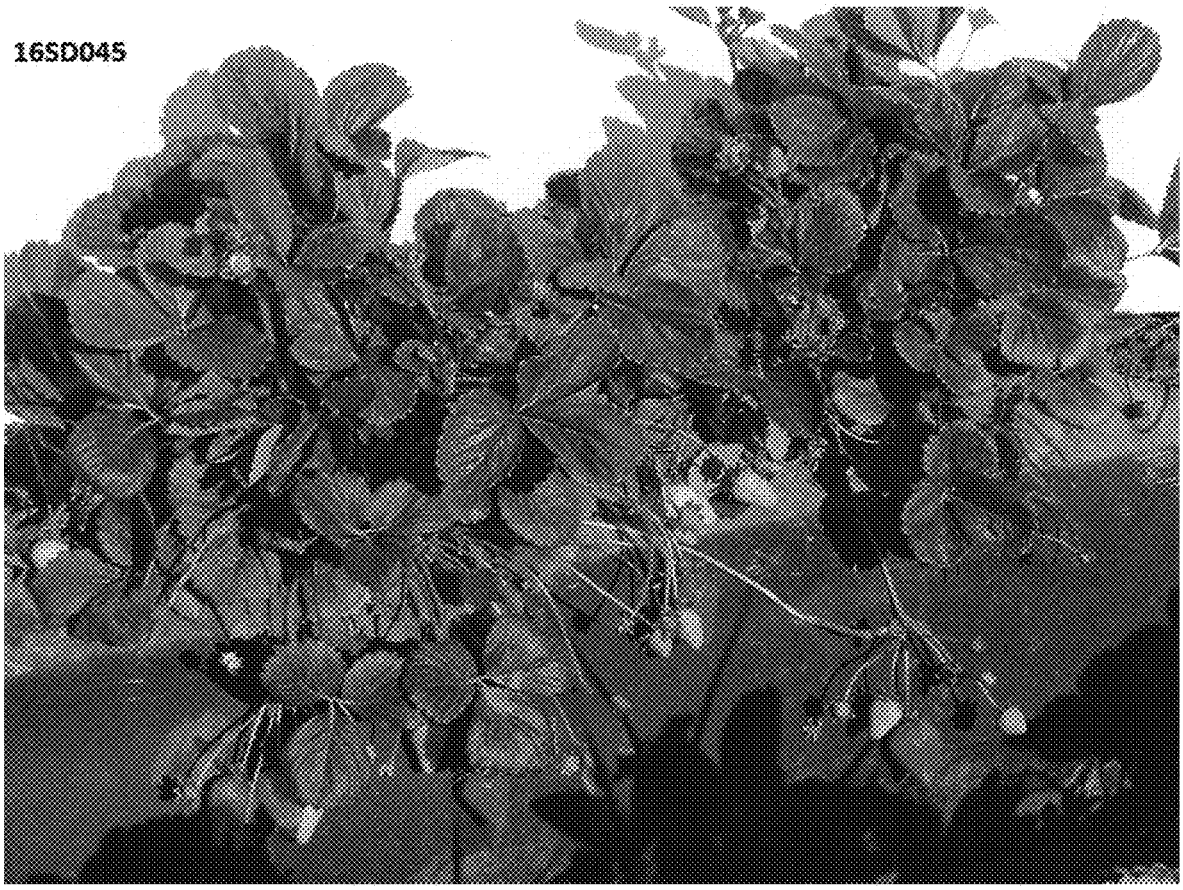
FIG. 3 depicts general plant and fruiting characteristics of 'UCD Victor'.
Figure 4:
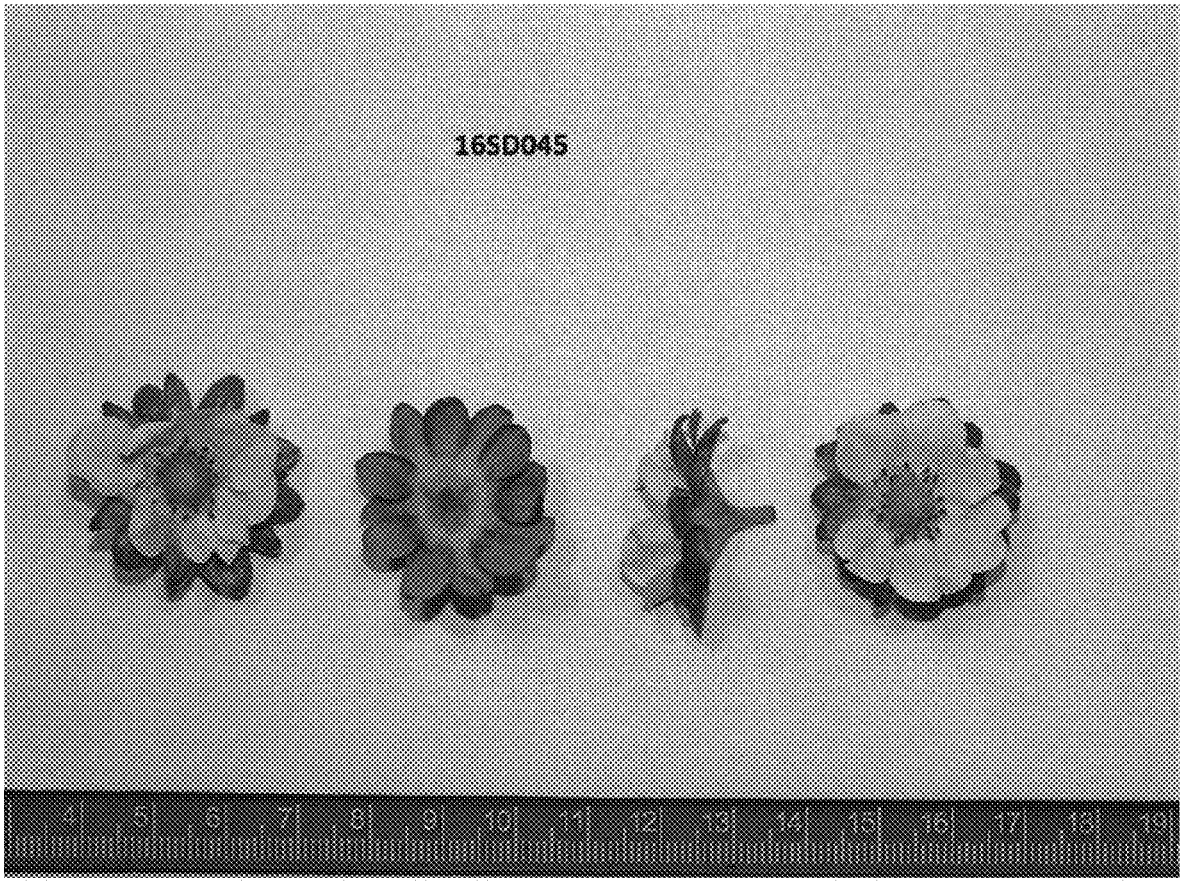
FIG. 4 shows representative flowers of the plant.
Figure 5:
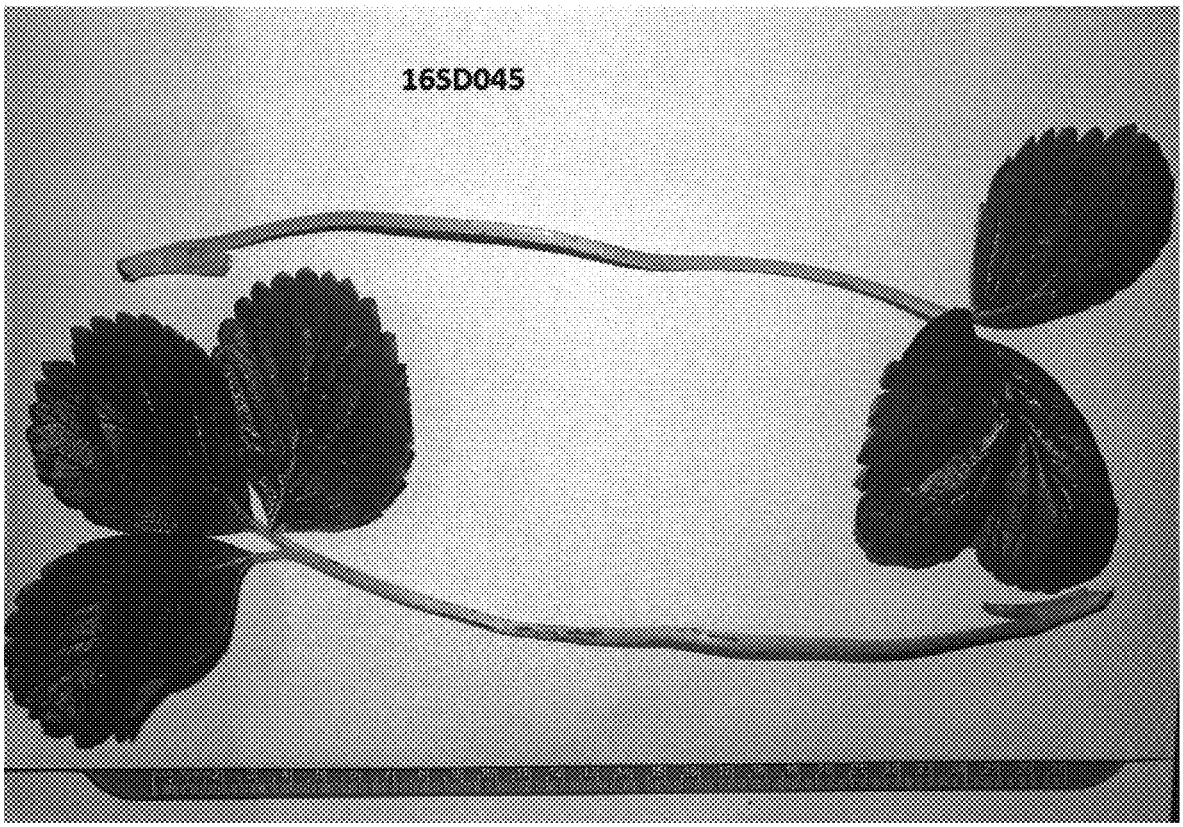
FIG. 5 shows representative leaves of the plant.
Figure 6:
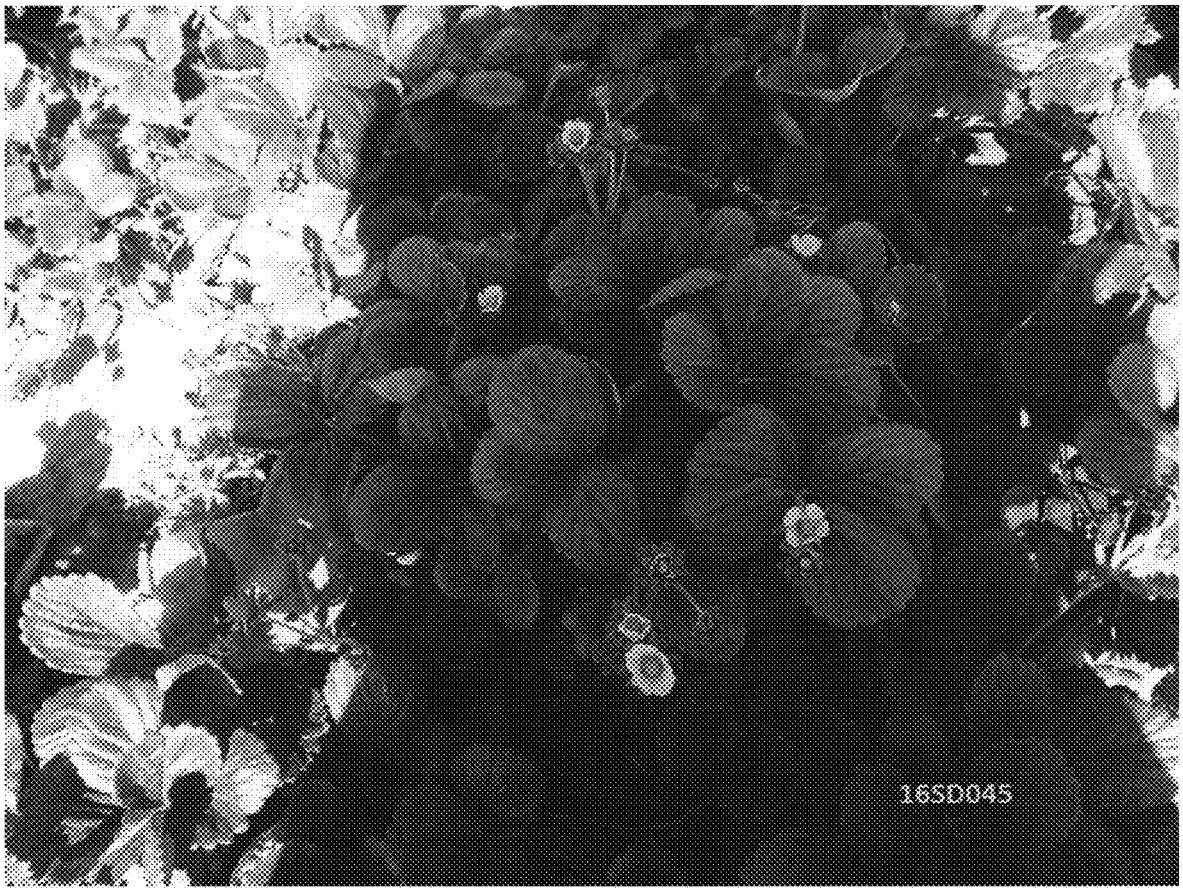
FIG. 6 depicts plant habit.

'UCD Victor' and comparison cultivars were asexually propagated in high-elevation nurseries in Dorris and Mcdoel, Calif. for field testing in 2015-2016, 2016-2017, and 2017-2018. Clones were harvested according to commercial planting schedules, which were calibrated by the number of chill hours required for optimum production in Oxnard, Calif. and Santa Maria, Calif.

'UCD Victor' and comparison cultivars were tested in replicated small-plot (24 plants/plot) yield trials in 2015-2016 in Oxnard and Santa Maria, Calif. Cultivar testing in the small-plot yield trials was performed as follows. Fruit was harvested once or twice per week over the spring and summer growing season: Dec. 24, 2015 to Jun. 2, 2016 in Oxnard, Ca. (49 harvests) and Feb. 14, 2016 to Jun. 27, 2016 in Santa Maria, Calif. (34 harvests). 'UCD Victor' was selected on the basis of fruit firmness, appearance, and size, flavor, and cumulative marketable fruit yield for a second year (2016-17) of replicated testing in small-plot yield trials in Oxnard and Camarillo, Calif. (Tables 1-2). Fruit was harvested once or twice per week over the growing season: Dec. 10, 2016 to Apr. 27, 2017 in Oxnard, Calif. (36 harvests) and Dec. 14, 2016 to May 15, 2017 in Camarillo, Calif. (26 harvests). To highlight differences among cultivars, the yield data were displayed in four ways: (a) per plant yields for individual harvests for each location×year combination for 'UCD Victor', 'Fronteras', 'Petaluma', and 'San Andreas'; (b) per plant cumulative marketable yields for 'UCD Victor', 'Fronteras', 'Petaluma', and 'San Andreas'; (c) per plant cumulative marketable yields for the cultivars tested in Oxnard and Santa Maria in 2015-16; and (d) per plant cumulative marketable yields tested in both years and locations.

Table 1 shows cumulative marketable yield (g/plant) for 'UCD Victor' compared to that for 'Fronteras', 'Petaluma', and 'San Andreas' in small-plot yield trials in Oxnard and Santa Maria, Calif. in 2015-2016; and Oxnard and Camarillo, Calif. in 2016-2017.

Table 2 shows statistical significance of differences between cumulative fruit yield and fruit weight for 'UCD Victor' and 'Fronteras', 'Petaluma', and 'San Andreas' in small-plot yield trials in Oxnard and Santa Maria, Calif. in 2015-2016; and Oxnard and Camarillo, Calif. in 2016-2017.

TABLE 1

Least-square means for cumulative marketable yield tested (g/plant).

| Cultivar | Oxnard 2015-16 | Santa Maria 2015-16 | Camarillo 2016-17 | Oxnard 2016-17 | Yield across Locations and Years (g/plant) |
|---|---|---|---|---|---|
| UCD Victor | 971.3 | 854.8 | 844.5 | 657.3 | 830.9 |
| Petaluma | 652.7 | 669.3 | 447.2 | 519.8 | 572.8 |
| San Andreas | 700.3 | 648.4 | 428.2 | 448.8 | 557.9 |
| Fronteras | 918.5 | 806.4 | 786.6 | 738.8 | 811.8 |

TABLE 2

Statistical significance (Pr > F) of differences between least square means for cumulative fruit yield (g/plant) and fruit weight (g/fruit) for 'Fronteras', 'Petaluma', and 'San Andreas' tested in small-plot yield trials in Oxnard and Santa Maria, CA in 2015-2016; and Oxnard and Camarillo, CA in 2016-2017.

| | Yield (g/plant) | | Fruit Weight (g/fruit) | |
|---|---|---|---|---|
| Comparison | Estimate | Pr > F | Estimate | Pr > F |
| UCD Victor-Fronteras | 19.1 | 0.7150 | −1.55 | 0.1821 |
| UCD Victor-Petaluma | 258.1 | <0.0001 | −0.80 | 0.4895 |
| UCD Victor-San Andreas | 273.0 | <0.0001 | 1.66 | 0.1529 |

There were significant differences among entries for cumulative marketable fruit yield ($p<0.0001$) and fruit weight ($p<0.0001$). Entry×environment interaction effects were significant for cumulative marketable fruit yield ($p<0.0001$) and fruit size ($p<0.0001$); however, entry rankings were fairly consistent and the best and worst performing cultivars were similar over locations and years (Tables 1 and 2). The broad-sense heritability for cumulative marketable fruit yield was 0.70 across locations and years. The broad-sense heritability for fruit weight was 0.59 across locations and years.

The cumulative marketable fruit yields of 'UCD Victor' were significantly greater than 'Petaluma' ($p<0.0001$) and 'San Andreas' ($p<0.0001$) and not significantly different from Fronteras ($p=0.72$) across years and locations (Tables 1 and 2).

There were no significant differences in fruit weight among the cultivars tested (least square mean differences across years and locations and associated p-values are shown in Table 2).

'UCD Victor' was selected for advanced testing in large-plot yield trials (150 plants/plot) in 2017-2018 (Tables 3 and 4). Several traits factored into the selection: resistance to one or more soil-borne pathogens, described below; high cumulative marketable fruit yield, fruit appearance; and resistance to bruising and post-harvest deterioration caused by harvest, handling, and storage. The production systems for large-plot yield trials included: low-input organic (Ventura) and high-input fumigated (Oxnard, Camarillo, and Santa Maria). These trials provided fruit for quality and post-harvest analyses.

TABLE 3

Least-square means (LSMs) for firmness, soluble solids concentration (SS), and titratable acid concentration (TA) for 'UCD Victor' and 'Fronteras' grown in four locations in 2017-18. LSMs were estimated from three harvest dates per location, one biological replication per harvest date, 12 sub-samples per harvest date for firmness, and three sub-samples per harvest date for SS and TA.

| Cultivar | Firmness (g force) | SS (%) | Titrable Acids (g/100 ml) | SS/TA |
|---|---|---|---|---|
| UCD Victor | 423.5 | 8.8 | 0.77 | 11.5 |
| Fronteras | 293.3 | 8.6 | 0.71 | 12.1 |

TABLE 4

Statistical significance (Pr > F) of differences between least square means for fruit firmness (g force) for 'UCD Victor' and 'Fronteras' tested in unreplicated large-plot yield trials in four locations in 2017-18.

| Comparison | Firmness Difference (g/force) | Pr > F | SS/TA Difference | Pr > F |
|---|---|---|---|---|
| UCD Victor-Fronteras | 130.2 | 0.0002 | −0.63 | 0.2394 |

To assess the quality of freshly harvested fruit, firmness (grams force), total soluble solids (SS) concentration, and titratable acid (TA) concentrations were measured from samples of fruit harvested on three dates from large-plot yield trials on farms in Oxnard, Camarillo, Ventura, and Santa Maria, Calif. in 2017-18 (Tables 3 and 4). Harvest dates were one month apart with one replication per harvest date, 12 sub-samples per replication for firmness, and three subsamples per replication for SS and TA. Firmness was quantified with a hand-held penetrometer measuring the grams of force needed to puncture the fruit. SS and TA concentrations were quantified with benchtop instruments. The SS to TA ratio provides a relative measure of sweetness.

'UCD Victor' produced the firmest fruits compared to 'Fronteras' (Tables 3 and 4) and, 'UCD Warrior' (data not shown). The SS/TA ratio for 'UCD Victor' was not significantly different from Fronteras (Tables 3 and 4).

To assess shelf-life, fruit weight (g/clamshell), SS, brightness (ordinal scale with 1=excellent to 5=unmarketable), liquid leakage (g/clamshell), and mold incidence(%) were quantified from samples of fruit harvested on two dates from each location with fruit stored under standard 4° C. conditions for 0, 7, and 14 days (Table 5). Harvest dates were one month apart with one replication per harvest date.

TABLE 5

Least-square means (LSMs) for fruit weight (g/clamshell), soluble solids concentration (SS), fruit brightness, liquid leakage, and mold formation for 'UCD Victor' and 'Fronteras' grown in four locations in 2017-18 and stored for zero to 14 days postharvest. LSMs were estimated from two harvest dates per location.

| Cultivar | Days Post-Harvest | Weight (g/clamshell) | Soluble Solids (%) | Bright-ness | Liquid Leakage (g) | Mold (%) |
|---|---|---|---|---|---|---|
| UCD Victor | 0 | 284.4 | 7.2 | 1.2 | 0.0 | 0.0 |
| UCD Victor | 7 | 272.8 | 6.5 | 3.3 | 0.8 | 0.0 |
| UCD Victor | 14 | 261.3 | 7.0 | 3.8 | 0.3 | 3.0 |
| Fronteras | 0 | 294.3 | 7.3 | 1.0 | 0.0 | 0.0 |

TABLE 5-continued

Least-square means (LSMs) for fruit weight (g/clamshell), soluble solids concentration (SS), fruit brightness, liquid leakage, and mold formation for 'UCD Victor' and 'Fronteras' grown in four locations in 2017-18 and stored for zero to 14 days postharvest. LSMs were estimated from two harvest dates per location.

| Cultivar | Days Post-Harvest | Weight (g/clamshell) | Soluble Solids (%) | Bright-ness | Liquid Leakage (g) | Mold (%) |
|---|---|---|---|---|---|---|
| Fronteras | 7 | 281.6 | 7.1 | 3.5 | 0.8 | 0.0 |
| Fronteras | 14 | 267.4 | 7.7 | 4.3 | 3.0 | 4.8 |

'UCD Victor' and 'Fronteras' maintained adequate marketability and visual appearance over 12-14 days of post-harvest storage, the industry standard (Table 5). Fruit weight and brightness significantly decreased and liquid leakage and mold formation increased among cultivars as post-harvest storage time increased, where brightness was measured on an ordinal 1 to 5 scale with 1=superior and 5=inferior (Table 5). Soluble solids concentrations were not significantly different between 'UCD Victor' and 'Fronteras' over 14 days of post-harvest storage.

Disease Resistance Evaluation

'UCD Victor' and additional cultivars were screened for resistance to *Fusarium* wilt, *Verticillium* wilt, *Macrophomina*, and *Phytophthora* crown rot in Davis, Calif. field experiments between 2015 and 2018. These included 2015-16 and 2016-17 *Fusarium* wilt screening experiments with 480 to 960 entries, a 2015-16 *Macrophomina* experiment with 960 entries, 2016-17 and 2017-18 *Verticillium* wilt experiments with 480 to 960 entries, and a 2017-18 *Phytophthora* crown rot experiment with 480 entries. Entries were arranged in randomized complete blocks experiment designs with four single-plant replications per entry. The 2015-16 experiments were planted in virgin soil in Davis, Calif. The 2016-17 and 2017-18 experiments were planted in fumigated soils in Davis, Calif. For each experiment, plants were artificially inoculated with the respective pathogen and phenotyped for disease symptoms on an ordinal scale, where 1=highly resistant (symptomless), 2=resistant, 3=intermediate, 4=susceptible, and 5=highly susceptible (dead). Within each experiment, plants were phenotyped at six different time points to study changes in the phenotypic distributions and quantify the progression of disease symptoms over time.

'UCD Victor' was highly resistant to *Fusarium* wilt (1.0 on scale) and heterozygous for $Fw_1$, a dominant resistance gene. The *Fusarium* wilt resistance score was not significantly different from the score for 'Fronteras' (1.1).

'UCD Victor' was susceptible to *Verticillium* wilt (4.3 on scale),and was significantly different from 'Fronteras' (p=0.38), which was 2.9 on scale.

'UCD Victor' was moderately resistant to *Phytophthora* crown rot (2.4 on scale) and susceptible to *Macrophomina* (5.0 on scale).

BOTANICAL DESCRIPTION

The following botanical descriptors are characteristic of 'UCD Victor'. The descriptors were collected from two different sites in May 2017 in Santa Maria, Calif. Colors are designated with reference to The Royal Horticultural Society (R.H.S.) Colour Chart, Sixth Edition, 2015. The characteristics of 'UCD Victor' may vary in detail, depending upon environmental factors and culture conditions.

Growth habitat: Semi-upright Plant height average of 30 cm. Plant spread average of 45 cm.
Density of foliage: Medium.
Vigor: Medium.
Position of inflorescence in relation to foliage: Same level.
Number of stolons: Average of 12.
Stolon, anthocyanin coloration: 61B Stolon, density of pubescence: Sparse.
Leaf size: Medium.
Leaf color: Adaxial 137A, Abaxial 148B.
Leaf blistering: Medium.
Leaf glossiness: Medium glossy.
Leaf variegation: Absent.
Terminal leaflet, length in relation to width: Average of 92 mm long and 63 mm wide.
Terminal leaflet, shape of base: Acute.
Terminal leaflet, margin: Crenate.
Terminal leaflet, shape in cross section: Concave.
Petiole, length: Average of 10 cm.
Petiole, attitude of hairs: Horizontal.
Stipule, anthocyanin coloration: Core color 144D, Margin color 143A (absent or very weak).
Inflorescence, number of flowers: Medium.
Pedicel, attitude of hairs: Horizontal.
Pedicel, anthocyanin coloration: 61B.
Flower diameter: Average of 25 mm.
Flower, arrangement of petals: Touching.
Flower, size of calyx: Calyx diameter average of 29 mm.
Color of calyx: 137A.
Flower stamen: Present.
Number of stamens per flower: Average of 23.
Number of sepals per flower: Average of 10.
Petal, length in relation to width: Equal, Average of 10 mm long and 10 mm wide.
Petal, color of upper side: NN155B.
Petal, color of lower side: NN155B.
Number of petals per flower: Average of 5.
Fruit, length in relation to width: Average of 52 mm long and 40 mm wide.
Fruit size: Average of 28 grams through the season for both primary and secondary fruit.
Fruit shape: Conical.
Fruit, difference in shape of terminal and other fruits: None or very slight.
Fruit color: 46B.
Fruit, evenness of color: Even or very slightly uneven.
Fruit glossiness: Strong.
Fruit, evenness of surface: Even or very slightly uneven.
Fruit, width of band without achenes: Absent or very narrow.
Fruit, positions of achenes: Below surface.
Achene color: 4A.
Fruit, position of calyx attachment: Inserted.
Fruit, attitude of sepals: Upwards.
Fruit, diameter of calyx in relation to fruit diameter: Same size.
Fruit, adherence of calyx: Medium.
Fruit firmness: Firm.
Fruit, color of flesh (excluding core): 40B.
Fruit, color of core: 31D.
Fruit cavity: Average of 5.2 mm.
Time of beginning of flowering: Early, start in January to May.
Time of beginning of fruit ripening: Early, starts in February to June.
Type of bearing: Not remontant.

PLANT AND FOLIAGE COMPARISONS

Fruiting plants of 'UCD Victor' are slightly taller than 'Fronteras', 'Petaluma' and 'San Andreas'. The spread is also wider than all 3 of the comparative cultivars. Leaves (including petioles) for 'UCD Victor' are shorter than 'Fronteras' and 'San Andreas', but longer than 'Petaluma'. Color for the upper and lower levels of the leaves of 'UCD Victor' are darker green than all 3 comparative cultivars. Serrations at midseason are more pointed than 'Fronteras' and more similar in shape and number to 'Petaluma' and 'San Andreas'. The stipule length of 'UCD Victor' is longer than all three comparative cultivars. Stolon production of 'UCD Victor' is greater than 'San Andreas', but less than for 'Fronteras' and 'Petaluma'.

FLOWERING AND FRUITING COMPARISONS

'UCD Victor' is similar to other California short day cultivars (e.g. 'Fronteras' and 'Petaluma') in that it will flower over an extended period into spring and early summer, given appropriate temperature and horticultural conditions. With most planting treatments, 'UCD Victor' flowers slightly later than the 3 comparative cultivars. The primary flowers for 'UCD Victor' are similar in size to the comparative cultivars with a calyx that is distinctly larger relative to the corolla on the primary fruit. The sepals for 'UCD Victor' are shorter than 'San Andreas' but similar in length to 'Fronteras' and 'Petaluma' and distinctly narrower than all 3 comparative cultivars. The calyx of 'UCD Victor' is variable (reflex to flat) more similar to 'Fronteras' and 'San Andreas', less reflexive than 'Petaluma'. The fruit shape of 'UCD Victor' can vary through the season, but is generally a long conic fruit similar to the fruit of 'San Andreas', the more medium conic fruit of 'Petaluma' and 'Fronteras'. External fruit color for 'UCD Victor' is darker red than both 'Fronteras' and 'Petaluma'. The internal fruit color of 'UCD Victor' is similar to 'Fronteras', but lighter than 'Petaluma'.

Achenes of 'UCD Victor' are indented in the fruit, comparatively similar to the fruit of 'Petaluma', but more indented than 'Fronteras' and 'San Andreas'.

What is claimed is:

1. A new and distinct cultivar of strawberry plant having the characteristics substantially as described and illustrated herein.

* * * * *